US008303602B2

(12) United States Patent
Biedermann et al.

(10) Patent No.: US 8,303,602 B2
(45) Date of Patent: Nov. 6, 2012

(54) INSTRUMENT FOR ASSEMBLING A BONE ANCHORING DEVICE (75) Inventors: Lutz Biedermann, VS-Villingen (DE); Wilfried Matthis, Weisweil (DE); Jürgen Harms, Karlsruhe (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 605 days.

(21) Appl. No.: 12/424,436

(22) Filed: Apr. 15, 2009

(65) Prior Publication Data

US 2009/0264896 A1  Oct. 22, 2009

Related U.S. Application Data (60) Provisional application No. 61/047,062, filed on Apr. 22, 2008.

(30) Foreign Application Priority Data

Apr. 22, 2008 (EP) ..................................... 08007795

(51) Int. Cl.
*A61B 17/88* (2006.01)
(52) U.S. Cl. ....................................................... 606/104
(58) Field of Classification Search .................. 606/104, 606/306, 328, 265–274; 81/52
See application file for complete search history.

(56) References Cited

U.S. PATENT DOCUMENTS

| 4,092,753 | A | * | 6/1978 | Fuhrmann | ........................ | 7/158 |
| 6,835,196 | B2 | | 12/2004 | Biedermann et al. | | |
| 6,981,976 | B1 | * | 1/2006 | Schoenefeld | ................ | 606/104 |
| 2002/0143341 | A1 | * | 10/2002 | Biedermann et al. | ........... | 606/73 |
| 2003/0225408 | A1 | | 12/2003 | Nichols et al. | | |
| 2004/0102781 | A1 | * | 5/2004 | Jeon | ................................ | 606/73 |
| 2004/0215190 | A1 | * | 10/2004 | Nguyen et al. | .................. | 606/61 |
| 2004/0225292 | A1 | * | 11/2004 | Sasso et al. | ..................... | 606/73 |
| 2005/0038432 | A1 | * | 2/2005 | Shaolian et al. | ................ | 606/61 |
| 2005/0177166 | A1 | * | 8/2005 | Timm et al. | ..................... | 606/73 |

(Continued)

FOREIGN PATENT DOCUMENTS

EP         452623 A2  * 10/1991

(Continued)

OTHER PUBLICATIONS

European Search Report for European Application No. 08007795.1-2310, European Search Report dated Aug. 28, 2008 and mailed Sep. 11, 2008 (6 pgs.).

*Primary Examiner* — Kevin T Truong
*Assistant Examiner* — Zade Coley
(74) *Attorney, Agent, or Firm* — Christie, Parker & Hale, LLP (57) ABSTRACT An instrument for assembling a bone anchoring device includes a shank with a shaft section to be anchored in a bone and a engagement end, a head being separate from the shank and having a through bore, and a receiving part having a first end, a second end and a longitudinal bore extending from the first to the second end, the head being positionable within the bore at the second end. The instrument includes a holding portion arranged to hold a pin, which has a rod section with a length and a diameter suited to fit and extend at least through the bore of the head, and which has a free end portion extending from the rod section such as to project from the bore of the head when the pin is inserted, and configured to engage with the engagement end of the shank.

14 Claims, 7 Drawing Sheets

U.S. PATENT DOCUMENTS

| | | | |
|---|---|---|---|
| 2006/0079894 A1* | 4/2006 | Colleran et al. | 606/61 |
| 2006/0111715 A1* | 5/2006 | Jackson | 606/61 |
| 2006/0200149 A1* | 9/2006 | Hoy et al. | 606/72 |
| 2006/0247658 A1* | 11/2006 | Pond et al. | 606/104 |
| 2006/0253120 A1* | 11/2006 | Anderson et al. | 606/86 |
| 2007/0043378 A1 | 2/2007 | Kumar et al. | |
| 2007/0055240 A1* | 3/2007 | Matthis et al. | 606/61 |

FOREIGN PATENT DOCUMENTS

| | | |
|---|---|---|
| EP | 1 741 396 A1 | 1/2007 |
| EP | 1 925 263 A1 | 5/2008 |
| FR | 2 880 254 | 7/2006 |

* cited by examiner

INSTRUMENT FOR ASSEMBLING A BONE ANCHORING DEVICE

CROSS-REFERENCE TO RELATED APPLICATION(S)

The present application claims the benefit of U.S. Provisional Patent Application Ser. No. 61/047,062, filed Apr. 22, 2008, the contents of which are hereby incorporated by reference in their entirety, and claims priority from European Patent Application EP 08007795.1, filed Apr. 22, 2008, the contents of which are hereby incorporated by reference in their entirety.

BACKGROUND

The present application relates to an instrument for assembling a bone anchoring device, which includes a shank, a head being separate from the shank, and a receiving part having a first end, a second end and a longitudinal bore extending from the first to the second end, the head being positionable within the longitudinal bore at the second end.

Such a bone anchoring device is described, for example, in U.S. Pat. No. 6,835,196 B2, by the same applicant. The device is arranged to connect a screw with a rod. The shank of the screw and the head are formed as separate parts. The head is shaped as a spherical segment thus being adapted to be pivotably held in the receiving part for allowing a multiaxial arrangement of the device. One example disclosed relates to the shank which has a cylindrical shape while the separate head is provided with one or more slits and further with a cylindrical bore into which the cylindrical end portion of the shank can be inserted.

Another example of a bone anchoring device having a screw with a shank and a spherically segmented head, which is separate from the head, is disclosed in EP 1741396 A1, by the same applicant. The shank has a threaded section and an engagement end, which is of conical shape, wherein the diameter increases towards the free end. Similarly, the head has a bore which is of conical shape, wherein the respective cone angles may be the same.

The head according to EP '396 is also provided with one or more slits to enable an elastic widening of the diameter at the bottom opening of the bore, when the engagement end is inserted, whose end diameter is slightly larger than former diameter of the head. The widening is facilitated by a chamfer arranged at the edges of the engagement end. As a result of this configuration, the head may be clicked onto shank upon assembly wherein the conical shape allows for enhanced stability, once the head is clamped.

Another example of a bone anchoring device having a screw with a separate shank and head is disclosed in European Patent Application no. 06 024 232 not yet published. The spherically segmented head has a cylindrical shape similar to the example disclosed in U.S. '196 described above. However, for example, a ring opened by a slit is provided as an elastic projection positioned within a circumferential groove inside the bore of the head. The engagement end of the shank is also of cylindrical in shape and has substantially the same diameter as the bore of the head to be insertable therein. The engagement end has a corresponding circumferential groove that may receive the projection, which may thus snap into the groove upon insertion of the engagement end into the cylindrical bore of the head.

The separate provision of the shank and the head with respect to the screw makes it possible to assemble sets of bone anchoring devices, in which one head may be combined with shanks of various sizes, structure and material properties. This may reduce the costs of a set since the heads will generally have to satisfy strong requirements with regard to accuracy, stress and tension characteristics, selection of material, etc., while the shanks may be produced according to the specific needs in large number with slightly less accuracy. This becomes particularly valid in cases, where spherically segmented heads are used, which provide for multi- or polyaxial arrangements of bone anchoring devices.

Further, simple screwing-in of the bone screw into the bone may be accomplished followed by easily clicking the preassembled receiving part including the head onto the engagement end.

It has been observed, however, that the assembly of bone anchoring devices as described above may eventually become somewhat circumstantial, just when multi- or polyaxial arrangements are involved. For example, the bore of the head positioned inside the bottom opening of the receiving part may pivot in any direction away from the engagement end of the shank which can render the assembly as a difficult procedure.

Based on the foregoing, there is a need to improve and facilitate the assembly of bone anchoring devices, in particular where bone screws are provided which have separate shanks and heads.

SUMMARY

The instrument according to the disclosure provides for a holding portion and pin. The pin is structured to have a rod section and a free end portion which is adjacent to the rod section. The rod section and free end portion can be inserted into a bore of a head which can be preassembled within the longitudinal bore of a receiving part of a bone anchoring device. Consequently, the rod section extends through the bore of the head such that the free end portion may project from the bore of the head and from an opening of the receiving part. In this case, the bore of the head is aligned with a longitudinal direction of the pin.

This configuration, i.e., the instrument holding the receiving part, can be applied to a shank. According to one aspect, the holding portion has an external thread that may engage an internal thread of the receiving part, commonly used for screwing-in a fixation element, in order to hold the receiving part.

The free end portion of the pin engages with the engagement end of the shank. The receiving part including the head and pin is preassembled. The pin thereby—according to one specific embodiment—sits on a spring and is therefore able to move along the longitudinal axis. The pin's free end portion helps to easily engage with an engagement end (comprising for example a bore) of the shank. After contacting the, e.g., planar face of the shank with the pin, a small compressive force applied to the instrument and the receiving part results in an axial movement of the pin. In one embodiment, the pin is supported in the holding portion of the instrument by a spring force means. When increasing the force a final end-position is achieved, in which the engagement end of the shank is locked to the head. This allows to disengage and remove the instrument.

The rod section of the pin serves to align the bore of the head with the longitudinal axis of the shank and, according to one embodiment, further widens an elastic projection, for example an elastic ring, in or at the bore of the head, which provides for the click mechanism designed to protect the shank from falling out. The projection may be, e.g., an elastic ring as in EP '232, or a slotted segment of the head providing a conical shape as in EP '396.

According to the specific embodiment detailed below, due to the retracting movement of the pin, the engagement end of the shank may slide into the head without a necessity to repeatedly widen the projection. Hence the force necessary to apply the preassembled receiving part to the shank may be considerably reduced.

DETAILED DESCRIPTION

Figure 1:
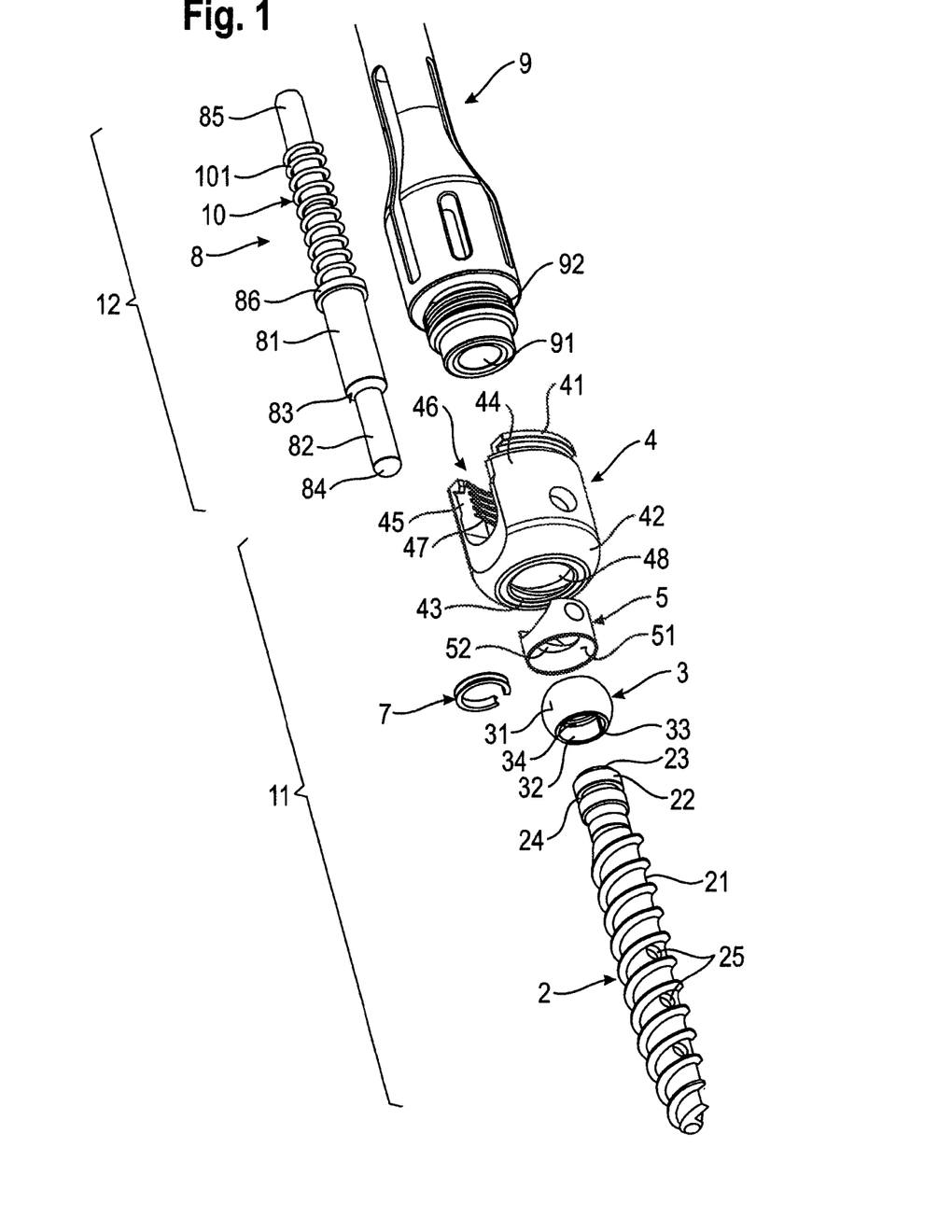
FIG. 1 shows an exploded view of a system having an instrument and a bone anchoring device according to an embodiment of the invention.

One embodiment of the instrument 12 and bone anchoring device 11 according to the invention is illustrated in the exploded view shown in FIG. 1. The bone anchoring device includes a shank 2, a head 3 separate from the shank 2, a partly opened ring 7, a pressure element 5 and a receiving part 4. Not illustrated in FIG. 1 are a rod and a fixation element (screw), which elements are to be applied only after the instrument 12 has been removed from the bone anchoring device 11.

The shank 2 has a threaded portion 21 intended to be anchored in a bone (not shown). The shank 2 further includes an engagement end 22, which in this specific embodiment is of substantially cylindrical shape, i.e., it has a constant outer diameter along its entire length except a groove 24 to be described below.

The head 3 has a substantially spherical outer surface 31, wherein a flattened surface may be provided on a top section thereof (not visible in the Figures). Further, a bore 32 extends through the head opening towards the top and bottom section thereof. The bore 32 in this specific embodiment is of cylindrical shape, the inner diameter of which corresponds to the outer diameter of the engagement end 22 of the shank 2. Still further, a slit 33 extends from the inner surface of the bore 32 to the outer spherical surface segment of the head. The slit 33 supports the clamping the engagement end 22 when the fixation element is screwed into the receiving part upon final fixation.

A circumferential groove 34 is also provided within the inner surface of the bore 32. The partly opened ring 7 serving as an elastic projection is provided in the groove 34. If no force is exerted on this ring 7, its diameter is smaller than the inner diameter of the bore 32. However, the ring may be widened to at least the inner diameter of the bore 32 upon exertion of a force which is directed radially outwards.

The pressure element 5 has on its bottom side a spherically shaped surface 51 which corresponds with the spherical outer surface 31 of the head 3. Due to this configuration, the head 3 is pivotable with respect to the pressure element in any direction prior to fixation. The device 11 thus refers to a multi- or polyaxial bone anchoring device. The pressure element 5 further has a center bore 52.

The receiving part 4 has a first end 41 and a second end 42. A longitudinal bore 48 extends between the first end 41 and the second end 42. The bore 48 is coaxial with a longitudinal axis of the receiving part 4 and may taper in a lower region towards the second end 42. An opening 43 formed at the second end 42 thus has a reduced diameter with respect to an upper region of the longitudinal bore 48 in order to position and clamp the head 3 after being inserted in the receiving part 4. The tapered profile may result in a spherically shaped surface which also corresponds with the outer spherical surface 31 of the head 3. However, the disclosure shall not be limited to the specific configuration of the receiving part.

The receiving part 4 further has a U-shaped recess 45 arranged to receive a rod (not shown). As a consequence two legs 44, 45 extend towards the first end 41. At the inner surface of the two legs 44, 45, an internal thread 47 is provided to engage with an outer thread of the fixation element (not shown)—and notably also with an outer thread 92 of a holding portion 9 of the instrument 12.

Figure 4:
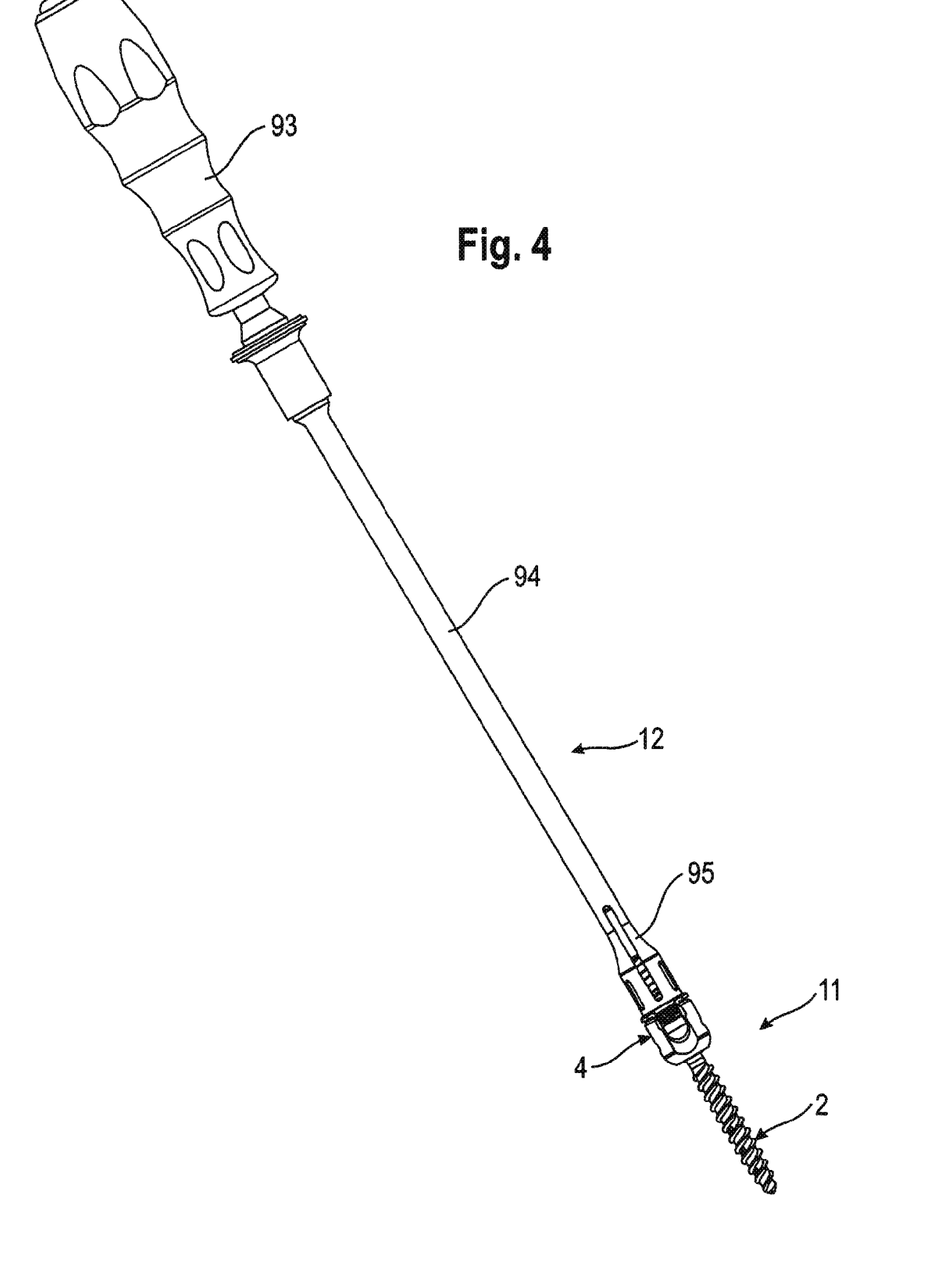
FIG. 4 shows a total side view of the system with the bone anchoring device being held by the instrument according to the embodiment shown in FIG. 1.

The instrument 12 includes the holding portion 9, a pin 8 and a spring force device 10. For example, the spring force device 10 may be a helical spring 101. A complete view of the instrument 12 holding the bone anchoring device 11 in an assembled state is provided in FIG. 4. The holding portion 9 includes a handle 93 that may be gripped manually by the surgeon or any other person that intends to assemble the device. An elongated rigid shaft 94 transfers forces exerted by the attending person to a pin-and-receiving-part holding section 95.

Section 95 therefore includes the external thread 92 as described above and a support bore 91 which receives and slideably supports a support section 85 of the pin 8.

The pin 8 may generally be fabricated from stainless steel or a biocompatible metal such as a Titanium alloy, a carbon filled PEEK (polymer), etc., and includes the support section 85, a rod section 81 and a free end portion 82, which herein is formed as an extended rod section. Portions 85, 81 and 82 are in this specific embodiment formed adjacent to each other in this order along the same longitudinal axis of the pin 8. The extended rod section has a tip 84 including a rounded profile. This profile serves to facilitate insertion of the pin into the bores 52, 32 of the head 3 and bore 26 of the engagement end 22 of the shank 2. The profile can also be otherwise tapered.

The free end portion 82, or extended rod section in this embodiment, serves to engage with the engagement end of the shank 2.

The rod section 81 has a diameter larger than that of the extended rod section. Between the rod section 81 and the extended rod section there is a transition portion 83 which has a tapered profile and which connects sections of different diameters. The angle of the tapered profile is preferably be set to 90°±30° with respect to the longitudinal axis of the pin. As will be described below, the transition portion 83 serves to widen the ring 7, when the pin 8 is inserted in the bore 32 of the head 3, and to abut on the end face 23 of the engagement end 22 of the shank 2.

Figures 2A, 2B:
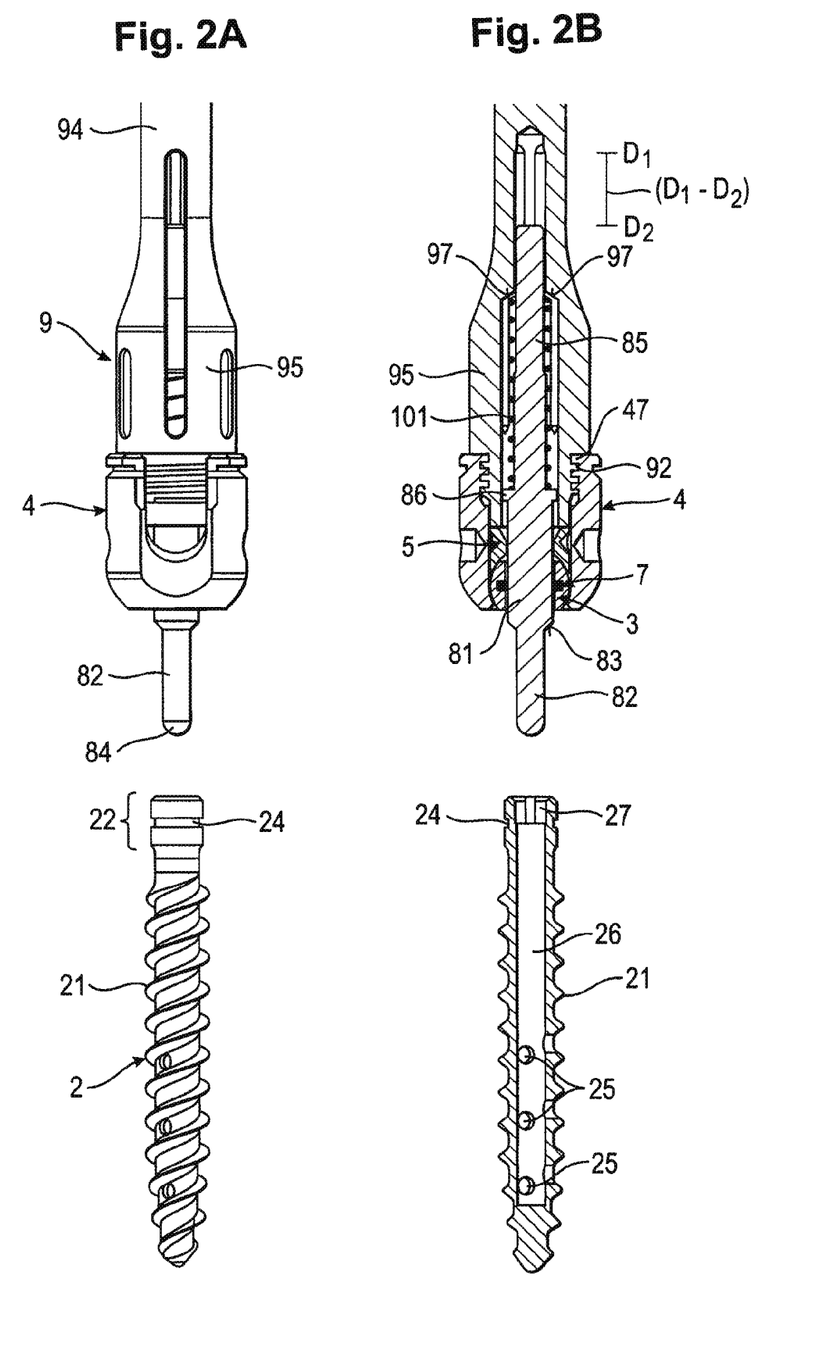
FIGS. 2A-B show a side view (FIG. 2A) and a sectional profile (FIG. 2B) of the embodiment shown in FIG. 1 in a state, where the receiving part is held by the instrument, but the shank is yet unloaded.

FIGS. 2A-B show in a side view (FIG. 2A) and a sectional profile (FIG. 2B) a state wherein the receiving part 4 is assembled with the head 3, the ring 7 and the pressure element 5, and wherein the pin 8 is inserted into bores 52, 32 of the pressure element 5 and the head 3, respectively, but prior to engagement of the shank 2. The receiving part 4 is thereby held by holding portion 9 of the instrument 12 via the external thread 92 being screwed into the internal thread 47. The helical spring 101 abuts on a stop 86 of the pin 8 and thus presses the pin 8 in axial direction towards the distal direction. The other end of the spring 101 is supported on a stop face 97 inside the support bore 91 of the holding portion 9.

It may be noted that the compression force may also be generated by any other suitable means such as for example pneumatic configurations provided inside the holding portion 9. Hence, the invention shall not be limited to the specific spring configuration described herein.

In a rest position shown in FIGS. 2A-B, the pin 8 attains the lowered end position D1 due to the compression or resilient force of the spring wherein the rod portion extends through the bores 52 and 32, and the free end portion 82 projects from the opening 43 of the receiving part 4. The rod section 81 has a diameter that in this embodiment corresponds to the inner diameter of the center bore 52 of the pressure element.

As a result, when in operation the instrument is first applied to the receiving part, the pin 8 is advantageously centered along the longitudinal central axis of the receiving part 4. Further, the rod section 81 has a diameter that also corresponds to the inner diameter of the bore 32 of the head 3. As a result, the bore 32 of the head 3 is advantageously aligned along the longitudinal central axis of the receiving part 4.

Figure 3A:
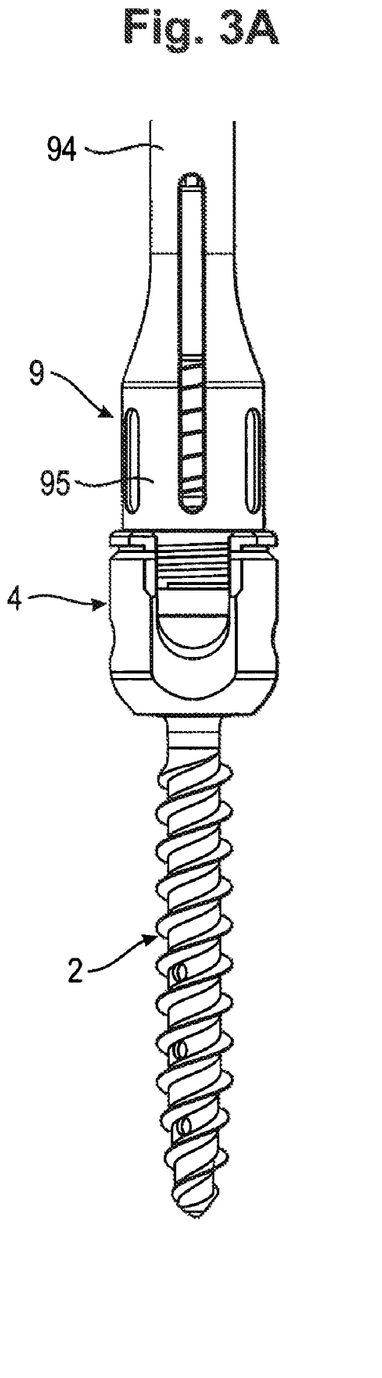
FIGS. 3A-B show the same as in FIGS. 2A-B, respectively, but in a state, where the shank is clicked to the receiving part.
Figure 3B:
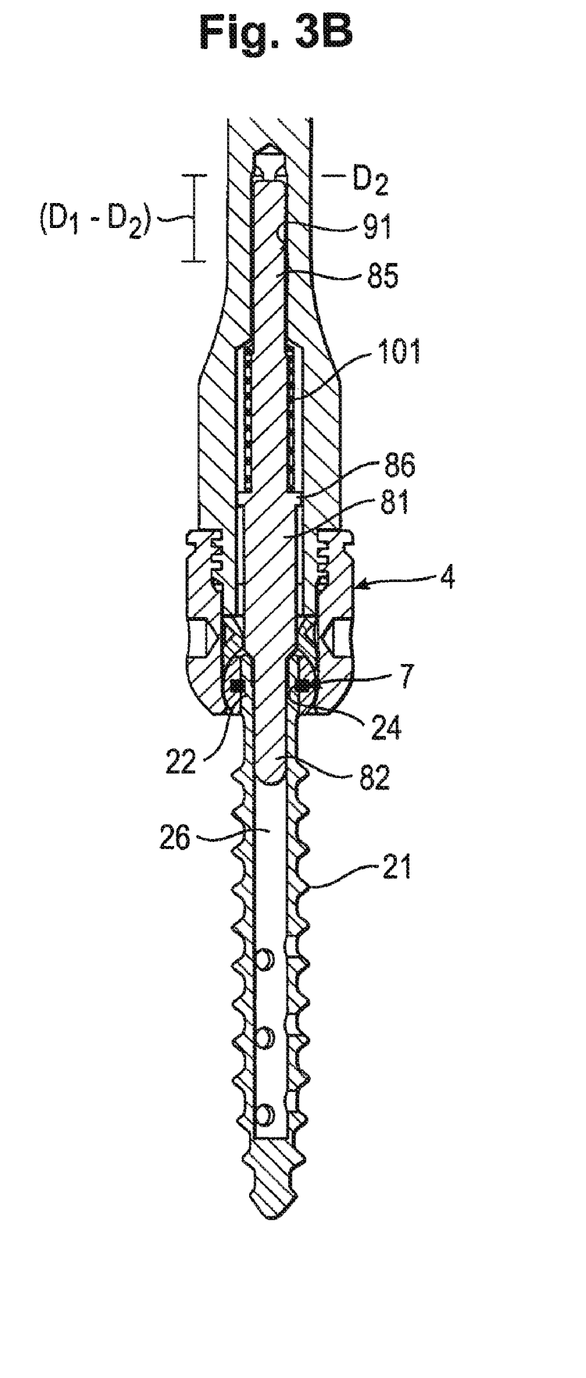

FIGS. 3A-B show the same configuration as in FIGS. 2A-B, respectively, but, in a state wherein the shank 2 is loaded to the receiving part 4. In this state the pin 8 is in the retracted upper end position D2. Prior to that, the tip 84 and the free end portion 82 may enter longitudinal bore 26 of the shank 2 which opens as an engagement portion 27 at the engagement end 22. An inner diameter of the longitudinal bore 26 is equal to or slightly larger than that of the free end portion, such as to ensure proper alignment of the shank 2 with the longitudinal direction each of the pin 8 and the receiving part 4.

Upon further insertion of the pin 8, the transition portion 83 eventually abuts on the annular shaped end face 23 of the engagement end 22. As a result, when the attending person further exerts a pressure force via the handle 93 to the receiving part 4 and the pin 8, the pin 8 starts a retracting movement relative to the receiving part 4 fixed to the holding portion 9 against the resilient or compression force of the helical spring 101. This process is depicted in detail in FIGS. 5A-5D.

It may be noted that the engagement portion 27 of the shank 2 may simultaneously serve to engage the shank 2 with a hexagonally shaped screwing tool in order to screw the shank 2 into the bone prior to the steps described herein. In this case, the bore 26 has in an upper portion at the engagement end 22 a hexagonal shape.

The distance of the positions D1 and D2 between which the pin 8 is slideably moved is indicated in FIGS. 2 and 3. This distance is at least as large as the length of the bore 32 in order that the engagement end 22 of the shank 2 may enter the bore when the pin 8 is further retracted. More specifically, the distance is at least as large such that the groove 24 formed in the outer surface of the engagement end 22 may be snapped by the ring 7 arranged inside the bore 32.

In operation, assembly of the bone anchoring element 11 is started by inserting first the spherically segmented head 3 already including the ring 7 into the receiving part 4, followed by inserting the pressure element 5. Next, the instrument 12 is applied to the receiving part 4 from the side of the first end 41 thereof. Initially, the tip 84 and the free end portion 82 enter the center bore 52 of the pressure element 5. The tip 84 then also enters the bore 32 of the head 3, which until then may be misaligned. It is then proceeded with the insertion movement wherein the tip 84 starts to leave the bore 32 and opening 43, while the transition portion 83 enters first the bore 52 and then the bore 32. Both the pressure element 5 and the head 3 are now aligned with respect to the longitudinal axis of the instrument 12 and the receiving part 4.

Next, the external thread portion 92 of the holding portion 9 abuts on the legs 44, 45 at the first end 41 of the receiving part 4. The external thread 92 is then screwed into the internal thread 47. One then arrives at the situation depicted in FIG. 2 or 5A.

Subsequently, the receiving part 4 now held by the instrument 12 is applied to the shank 2. The application may be performed in situ, i.e., when the shank 2 is already screwed into the bone, or prior to surgery. However, in case of an in situ application a particular advantage arises in that since only moderate forces are applied, stress acting on the bone material can be relieved using this embodiment of the invention.

Figures 5A, 5B:
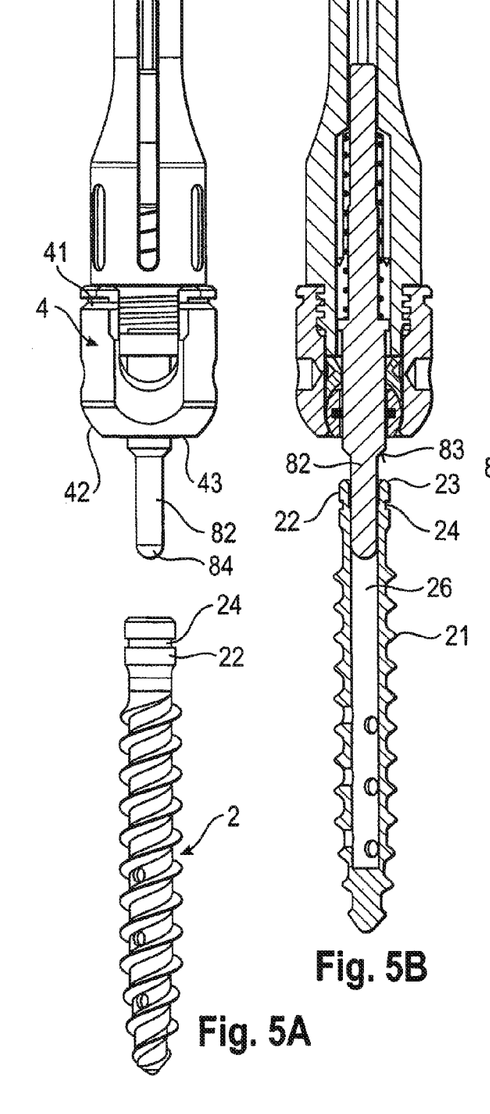
FIGS. 5A-D illustrates the steps of loading the shank to the receiving part according to the invention according to an embodiment of the method.

The tip 84 of the free end portion 82 is thereby inserted to the bore 26 which opens at the engagement end 22 of the shank 2. Upon further insertion to sufficient depth an alignment of the shank 2 with the longitudinal axis of the pin 8 is achieved (FIG. 5B).

Figures 5C, 5D:
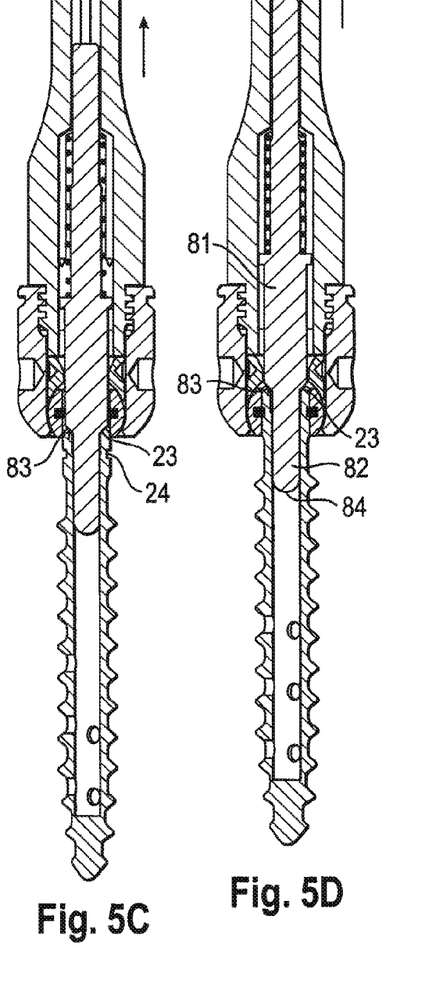

Eventually, the transition portion 83 abuts on the end face 23 of the engagement end 22. The pin then moves into the support bore 91 of the holding portion 9. This results in a compression force of the helical spring 10 (FIG. 5C). Thereby, the engagement end 22 of the shank enters the opening 43 of the receiving part 4 and the bore 32 of the head 3. Since the projecting ring 7 has been widened by the transition portion 83, substantially no widening force has to be exerted by the engagement end 22 when its end face 23 passes the ring 7, which stays widened until the groove 33 passes into which it then snaps. The shank is now temporarily locked.

The external thread 92 may then be unscrewed from the internal thread portion 47 of the receiving part 4 to remove the instrument. Thereby the pin returns sliding outwards under the compression force of the helical spring. Next a rod may be inserted into the U-shaped recess 46 of the receiving part and secured by a fixation element.

Figure 6A:
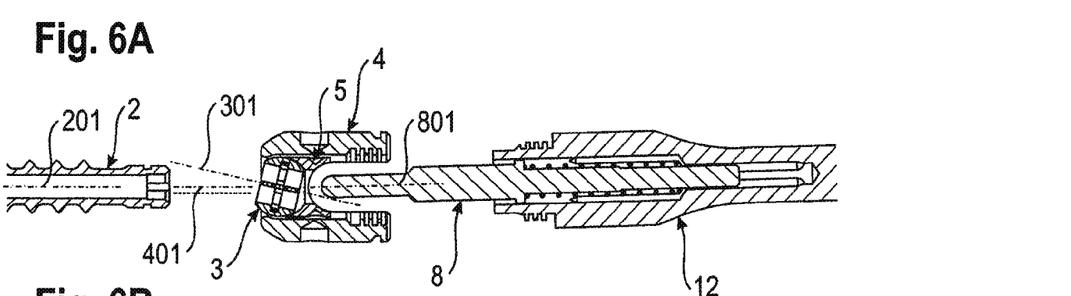
FIGS. 6A-D illustrate the steps of inserting the pin into the receiving part and the bore of the head according to the embodiment.
Figures 6B, 6C, 6D:
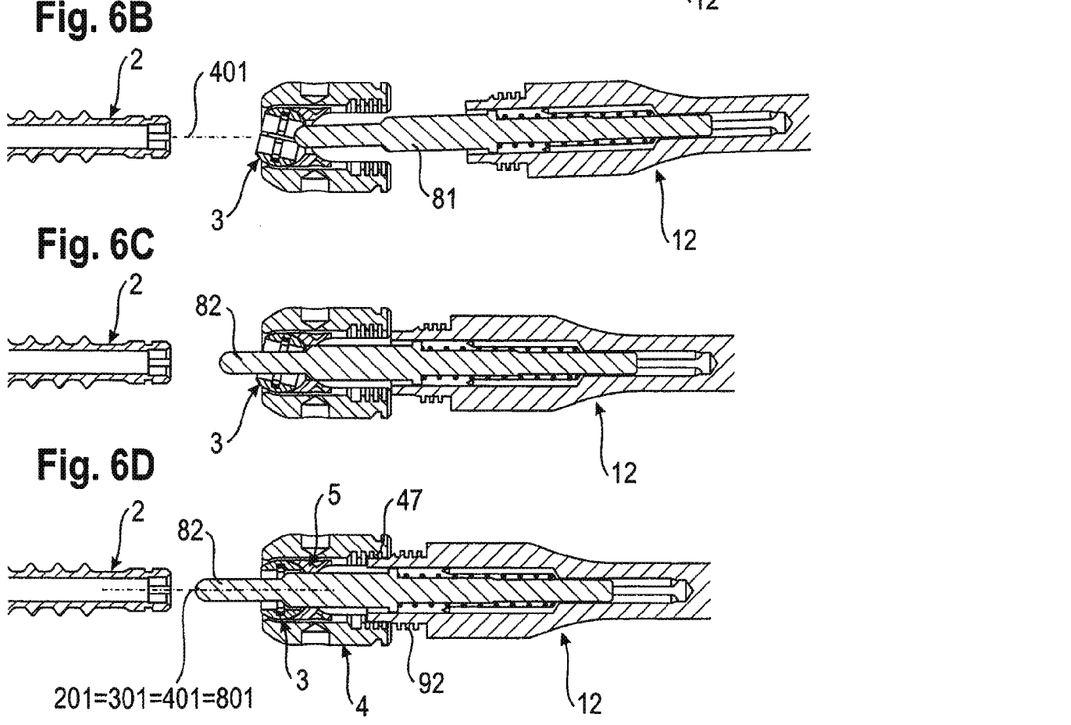

FIG. 6A-6D illustrate in detail the steps of aligning the head 3 with longitudinal axes 401, 801 of the receiving part and the pin, respectively, with regard to the above described embodiment. In FIG. 6A, the pin 8 is inserted in the pre-assembled receiving part 4. In this situation axes 401, 801 of both components not yet aligned with each other, and the longitudinal axis 301 of the spherical segmented head is strongly inclined to both axes 401, 801. In FIG. 6B, the tip of the pin 8 enters the bore 32 of the head 3. The head 3 starts to be slightly rotated due to the engagement by the pin 8.

In FIG. 6C, the transition portion 83 and subsequently the rod portion 81 enter the center bore of the pressure element and thereafter also bore 32 of head 3. As a consequence, the head 3 is centered and its longitudinal axis 301 is aligned with axes 401, 801 (FIG. 6D). In a next step shown in FIGS. 5B-5D, the longitudinal axis 201 of the shank 2 is also aligned with axes 301, 401, 801, when the free end portion 82 enters the bore at the engagement end 22 of the shank 2.

A specific embodiment has been described herein. It becomes clear to the person skilled in the art that other features yielding similar functions may be employed instead of those detailed herein. It also becomes clear that other specific features shown herein may be omitted, while the desired functions may still be achieved. For example, the figures show a shank 2 having a radial bore 26, which is connected to radial bores 25 intended to provide bone cement into the bone in order to improve bone growth in a vicinity of the shank. However, the present instrument achieves its functions as well if the shank merely had a short longitudinal bore 26 having length corresponding to that of the free end portion 82 of the pin 8, i.e., without necessitating radial bores 25.

It is noted that the through-hole as set forth in the appended claims may be represented by a single bore 32 having a substantially constant diameter over its entire length. The bore 32 of the embodiment described above has a diameter corresponding to that of a section of the pin 8 and to that of the engagement end 22 of the shank 2 (bone screw). However, this limitation may not be required according to the invention.

Figure 7:
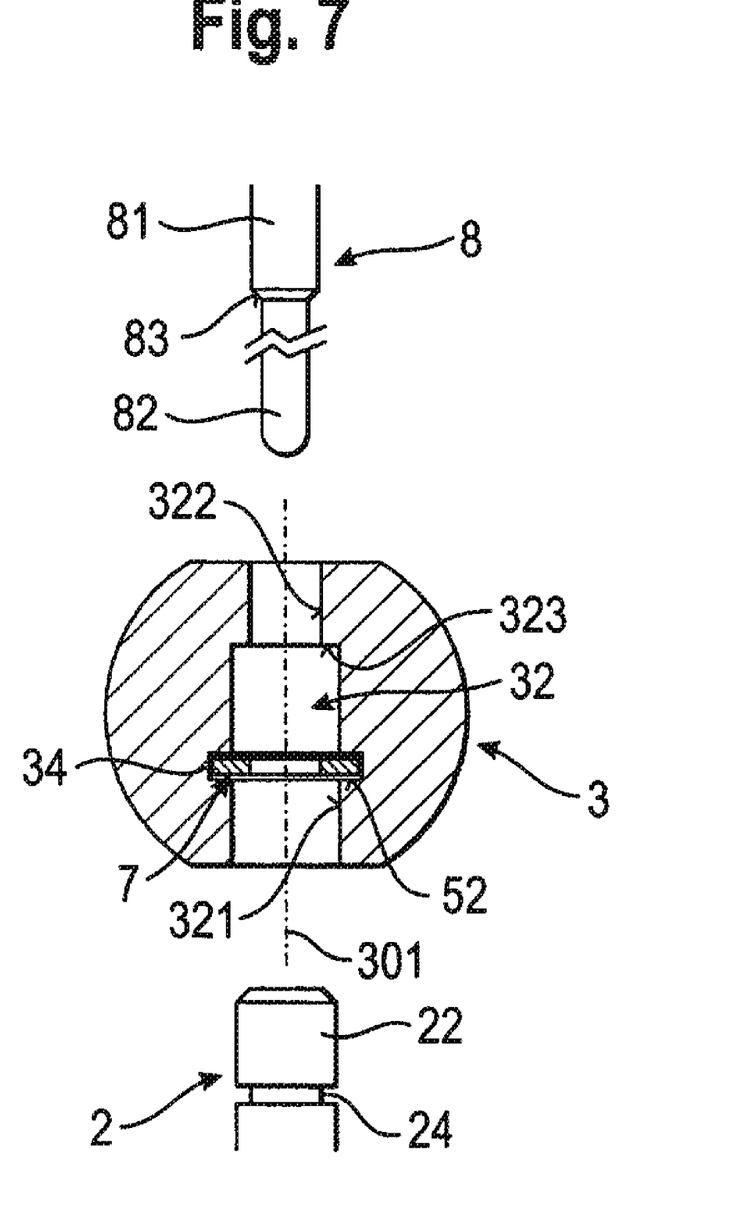
FIG. 7 shows a modification of the head 3 according to another embodiment.

For example, the through-hole of the head 3 may comprise a first bore 321 with a first diameter, into which the engagement end 22 of the shank fits, and a second bore 322 coaxial with and adjacently extending from the first bore 321, into which the pin 8 is inserted prior to entering the second bore. The situation is schematically depicted in FIG. 7. The engagement end 22 of the shank according to the modification of the embodiment according to FIG. 7 may for example abut on a stop face 323, when the elastic ring simultaneously snaps into the groove.

Further, the engagement end 22 and the bore 32 of the head have been described as being cylindrical, wherein a projection and a groove provide a click mechanism. However, the invention may similarly be embodied with the engagement end and the bore arranged in conical shape such as in EP '396.

Further the head 3 may also comprise a slit (not shown) which extends along the entire length in the direction of its longitudinal axis, whereby it elastically opens the head 3 on one side thereof, reaching from the inner surface of the through-hole or bore(s) 32 to the outer spherically shaped surface 31 of the head 3.

Further, the engagement portion at the engagement end of the shank, which also serves to be engaged by a screwing-in tool, may be of any other type than a polygonal or hexagonal bore. For example, the engagement portion may be of a cross-slot type, etc. Or a polygonal or hexagonal shaped bore is formed in the free end portion of the pin while the engagement end has a corresponding protrusion including a suitable diameter.

What is claimed is:

1. A system for assembling a bone anchoring device, comprising:
   a bone anchoring device comprising:
      a shank having a shaft section to be anchored in a bone and an engagement end, the shank having a longitudinal axis;
      a head being separate from the shank and having a through bore; and
      a receiving part having a first end, a second end defining a longitudinal axis, and a longitudinal bore extending from the first to the second end, the head being positionable within the bore of the receiving part at the second end; and
   an instrument comprising:
      a holding portion and a pin, the holding portion configured to hold the pin;
      the pin comprising:
         a rod section having a length and a diameter configured to it and extend at least through the bore of the head when the pin is inserted therein; and
         a free end portion extending from the rod section such as to project from the bore of the head, and configured to engage with the engagement end of the shank and project past the engagement end of the shank to align the longitudinal axis of the receiving part with the longitudinal axis of the shank.

2. The system according to claim 1, wherein the diameter of the rod section of the instrument is equal to or slightly less than the diameter of the through bore of the head.

3. The system according to claim 1, wherein:
   the engagement end of the shank is formed of a substantially tubular shape and includes a longitudinal bore which has a cylindrical or polygonal sectioned surface and which has an inner diameter; and
   the diameter of the free end portion of the pin is equal to or slightly less than the inner diameter of the longitudinal bore formed in the engagement end of the shank.

4. The system according to claim 1, wherein:
   an inner surface of the through bore of the head is of substantially cylindrical shape and includes an inner circumferential grove configured to receive a projection configured to be elastically widened by a transition portion of the pin; and
   the outer surface of the engagement end of the shank is provided with an outer circumferential groove configured to receive the projection upon insertion of the engagement end into the bore of the head.

5. The system according to claim 1, wherein the head of the bone anchoring device comprises in at least one segment on an outer spherical surface to enable multiaxial pivoting movement inside the receiving part prior to fixation.

6. A system according to claim 1, wherein the bone anchoring device further includes a pressure element configured to transfer pressure exerted from at least one of a fixation element and a rod to the head in order to clamp the head, the pressure element including a center bore.

7. A system according to claim 4, wherein an outer diameter of the engagement end of the shank is substantially the same as the diameter of the rod section of the pin in order to provide a smooth sliding movement of the projection in the bore of the head from an outer surface of the rod section to an outer surface of the engagement end.

8. The system according to claim 1, wherein the pin is configured to slidably move with respect to the holding portion along a longitudinal axis of the instrument against a resilient force configured to be exerted between the holding portion and the pin when the pin engages with the shank.

9. The system according to claim 1, wherein the free end portion has a diameter smaller than a diameter of the rod section, and wherein a transition portion between the rod section and the free end portion includes at least one of a conical and tapered profile configured to widen a diameter of an elastic projection provided in the bore of the head or to abut on an end face of the engagement end of the shank.

10. The system according to claim 1, wherein the holding portion comprises an outer thread arranged to be screwed into an inner thread near the first end of the receiving part of the bone anchoring device.

11. The system according to claim 1, wherein the pin is slidable relative to the holding portion from a resting position to a compressed position, and wherein the distance between the resting position and the compressed position is equal to or larger than a length of the through-hole of the head.

12. A method of assembling a bone anchoring device with an instrument, the bone anchoring device comprising a shank having a longitudinal axis, a shaft section to be anchored in a bone and an engagement end, a head being separate from the shank and having a through bore, and a receiving part having a first end, a second end defining a longitudinal axis, and a longitudinal bore extending from the first to the second end, the head being positionable within the bore of the receiving part at the second end, the instrument comprising a holding portion and a pin, the holding portion configured to hold the pin, the pin comprising a rod section having a length and a diameter configured to fit and extend at least through the bore of the head when the pin is inserted therein, and a free end portion extending from the rod section such as to project from the bore of the head, and configured to engage with the engagement end of the shank and project past the engagement end of the shank to align the longitudinal axis of the receiving part with the longitudinal axis of the shank, the method comprising:

inserting the pin into and through the bore of the head such that the free end portion projects from an opening of the longitudinal bore, and the head is aligned with the pin;

engaging the free end portion of the pin with the engagement end of the shank to align the longitudinal axis of the receiving part with the longitudinal axis of the shank;

moving the pin engaged with the shank relative to the receiving part along the longitudinal axis of the receiving part to retract the pin and to insert the engagement end of the shank into the bore of the head positioned within the opening of the longitudinal bore;

locking the engagement end in the bore of the head; and removing the instrument with the pin from the receiving part.

13. The method according to claim 12, wherein the shank is first anchored in a human bone prior to engaging the shank with the engagement end.

14. The method according to claim 12, further comprising:

fixing the instrument to the receiving part after inserting the pin through the bore of the head in order to facilitate holding the receiving part with the instrument;

moving the pin in a direction along the longitudinal axis of the receiving part against a resilient force of a spring force device provided in the instrument after engaging with the engagement end; and     releasing the instrument from the receiving part prior to removing the instrument.

\* \* \* \* \*

UNITED STATES PATENT AND TRADEMARK OFFICE
CERTIFICATE OF CORRECTION

| | | |
|---|---|---|
| PATENT NO. | : 8,303,602 B2 | Page 1 of 1 |
| APPLICATION NO. | : 12/424436 | |
| DATED | : November 6, 2012 | |
| INVENTOR(S) | : Lutz Biedermann et al. | |

It is certified that error appears in the above-identified patent and that said Letters Patent is hereby corrected as shown below:

In the Claims

Column 7, Claim 1, line 63        Delete "it"
                                                               Insert -- fit --

Column 8, Claim 5, line 26        Delete "on"

Signed and Sealed this
Fifteenth Day of October, 2013

Teresa Stanek Rea
*Deputy Director of the United States Patent and Trademark Office*